(12) United States Patent
Sundström et al.

(10) Patent No.: US 8,802,033 B2
(45) Date of Patent: Aug. 12, 2014

(54) SLICING DEVICE

(76) Inventors: Erik Sundström, Danderyd (SE);
Elisabet Åkesson, Stockholm (SE);
Thomas Laurell, Lund (SE); Lars Wallman, Vollsjö (SE)

(*) Notice: Subject to any disclaimer, the term of this patent is extended or adjusted under 35 U.S.C. 154(b) by 342 days.

(21) Appl. No.: 12/598,769

(22) PCT Filed: Apr. 30, 2008

(86) PCT No.: PCT/SE2008/000302
§ 371 (c)(1),
(2), (4) Date: Nov. 4, 2009

(87) PCT Pub. No.: WO2008/136729
PCT Pub. Date: Nov. 13, 2008

(65) Prior Publication Data
US 2010/0136690 A1 Jun. 3, 2010

Related U.S. Application Data

(60) Provisional application No. 60/958,826, filed on Jul. 10, 2007.

(30) Foreign Application Priority Data

May 4, 2007 (SE) ...................................... 0701081
Jun. 7, 2007 (SE) ...................................... 0701380

(51) Int. Cl.
*A61B 10/00* (2006.01)

(52) U.S. Cl.
USPC ............. 422/536; 422/68.1; 422/50; 422/500

(58) Field of Classification Search
USPC .......................... 422/64–67, 500, 536, 50, 68
See application file for complete search history.

(56) References Cited

U.S. PATENT DOCUMENTS

| | | | |
|---|---|---|---|
| 5,197,483 A | 3/1993 | Rogalsky et al. | |
| 5,396,898 A | 3/1995 | Bittmann et al. | |
| 5,692,424 A * | 12/1997 | Wallace | ........................ 83/167 |
| 2002/0040872 A1 | 4/2002 | Bogoev et al. | |
| 2002/0197631 A1* | 12/2002 | Lawrence et al. | ................. 435/6 |
| 2008/0026464 A1* | 1/2008 | Borenstein et al. | ........... 435/395 |

FOREIGN PATENT DOCUMENTS

| | | |
|---|---|---|
| JP | 5-85405 | 11/1993 |
| JP | 2003/235543 | 8/2003 |
| JP | 2003-235543 | 8/2003 |
| WO | WO 93/01271 | 1/1993 |

OTHER PUBLICATIONS

Tumezei et al., "Low-Cost Microfilter for Red Blood Cell Membrane Stiffness Measurement Using Photosensitive BCB", *IEEE: Transducers*, 2003, p. 107-110.

(Continued)

*Primary Examiner* — Jyoti Nagpaul
(74) *Attorney, Agent, or Firm* — Merchant & Gould P.C.

(57) ABSTRACT

The invention relates to a biological microglia comprising at least two pores having a size adopted to allow cells, cell aggregates, tissue or other biological material to pass through said pores, and one or several slicing beams separating said pores from each other, wherein biological material is split/sliced/cleaved into at least two parts when passing said microgrid, a slicing device, an apparatus comprising said slicing device as well as the use of said microgrid, slicing device and apparatus.

6 Claims, 9 Drawing Sheets

(56) References Cited

OTHER PUBLICATIONS

Wallman et al., "Biogrid—a microfluidic device for large-scale enzyme-free dissociation of stem cell aggregates", *Lab on a Chip*, 11, 2011, p. 3241-3248.

European Search Report from EP Application No. 08 74 1875 dated Apr. 13, 2010.
Saha et al. "Comparison of enymatic and mechanical methods for the collection of bovine preantral follicles." *Animal Science*. vol. 74. 2002. pp. 155-161.

* cited by examiner

Slicing Unit, example no 2

Slicing Device, example with replaceable slicing unit

SLICING DEVICE

This application is a National Stage Application of PCT/SE2008/000302, filed 30 Apr. 2008, which claims benefit of Ser. No. 0701081-2, filed 4 May 2007 in Sweden, Serial No. 0701380-8, filed 7 Jun. 2007 in Sweden, and U.S. Ser. No. 60/958,826, filed 10 Jul. 2007 and which applications are incorporated herein by reference. To the extent appropriate, a claim of priority is made to each of the above disclosed applications.

FIELD OF INVENTION

The invention relates to a biological microgrid comprising at least two pores having a size adopted to allow cells, cell aggregates, tissue or other biological material to pass through said pores, and one or several slicing beams separating said pores from each other, wherein biological material is split/sliced/cleaved into at least two parts when passing said microgrid, a slicing device, an apparatus comprising said slicing device as well as the use of said microgrid, slicing device and apparatus.

BACKGROUND OF INVENTION

Immature cells, so called stem cells, progenitor cells or precursor cells, with the potential to develop into different types of mature cells, is the most promising strategy for restoring injured tissue.

Stem cells (used in this text to denominate all types of immature, multipotent cells) can be isolated from different sources. Embryonic stem cells are derived from surplus fertilized egg cells, fetal stem cells are isolated from embryonic/fetal tissue, adult stem cells are derived from adult tissue of different types, and tumors are used for cancer stem cells. These self-renewing cells are kept in cell culture systems and expanded, to provide a source for different experimental and clinical purposes. In addition to the culturing of stem cells, many mature cells also undergo cell division and can also be expanded in cultures maintained the same way as stem cells.

Cells are grown under conditions, which favor their survival and growth, either as adherent cultures (i.e. all cells adhere to the bottom of the cell culture flask or dish) or as free-floating cell aggregates. With time, the number of cells in each culture flask increases and eventually the cells have to be split into more cell culture flasks. Splitting the cells usually involves separating the cells into a homogenous suspension of single cells (dissociation). Dissociation is done mechanically by grinding, or by adding proteolytic enzymes. Alternatively the cell aggregates can be cut into smaller pieces without dissociating them. This method involves cutting the tissue with razor blades or scissors, which is very time consuming and prone to contamination.

Minimizing cell death throughout the entire process is a prerequisite for successful expansion of cells in culture. Dissociation always leads to some cell death, probably as a combined effect of the rupture of cell membranes during the dissociation and the demise of cells after re-seeding them as single cells. Depending on the strength of the bonds between cells, different cell types may be more prone to damage during dissociation. Optimizing this process is therefore important. Adding enzymes for the dissociation process also introduces a risk of contamination as well as the problem that low concentrations of enzymes can remain in cells used for cell therapy. In conclusion, it would be beneficial to develop methods that enhance the survival and expansion of cell cultures, while eliminating the use of exogenous enzymes.

There are other applications for which reproducible cutting or slicing of biological tissue is an important part of the procedure. So called organotypic cultures are established by using thin slices of tissue, typically 200-400 µm. These slices are maintained in culture systems to preserve the cellular organization of the organ which was used. These slices or prisms of tissue are also used for acute in vitro experiments, for example studying the change in metabolism upon exposing the tissue to a drug. The last few years we have also seen tissue slices being used in so called high-content screening, test systems utilizing large-scale testing of drugs and substances in complex cell systems such as organotypic cultures.

SUMMARY OF THE INVENTION

The invention relates to a biological material slicing device. Said slicing device belongs to a technology platform consisting of micro-grids, herein called microgrids, which are used to cut biological material into defined pieces. Said microgrid comprise at least two pores having a size adopted to allow cells, cell aggregates, tissue or other biological material to pass through said pores, and a slicing beam separating said pores from each other, wherein biological material is split/sliced/cleaved into at least two parts when passing said microgrid.

According to another aspect the invention relates to an apparatus containing said slicing device, this apparatus is used for cell cultures to slice aggregates of cells into aggregates of smaller size.

In a final aspect the invention relates to the use of said slicing device or said apparatus.

By providing a slicing device and said apparatus, it is possible to cut tissue, cell aggregates and other biological material in minute pieces of defined size, in a highly reproducible way and in large quantities. The technology can easily be implemented in fluidic systems to cut tissue or cell aggregates using automated procedures. The device described can be used for cell cultures to cut aggregates of stem cells, precursor cells, progenitor cells or mature cells by aspirating or ejecting them through the device, thereby avoiding enzymatic dissociation and the need for tryptic enzymes, as well as mechanical dissociation which is associated with considerable cell death.

DETAILED DESCRIPTION OF THE INVENTION

Definitions

Figure 1:
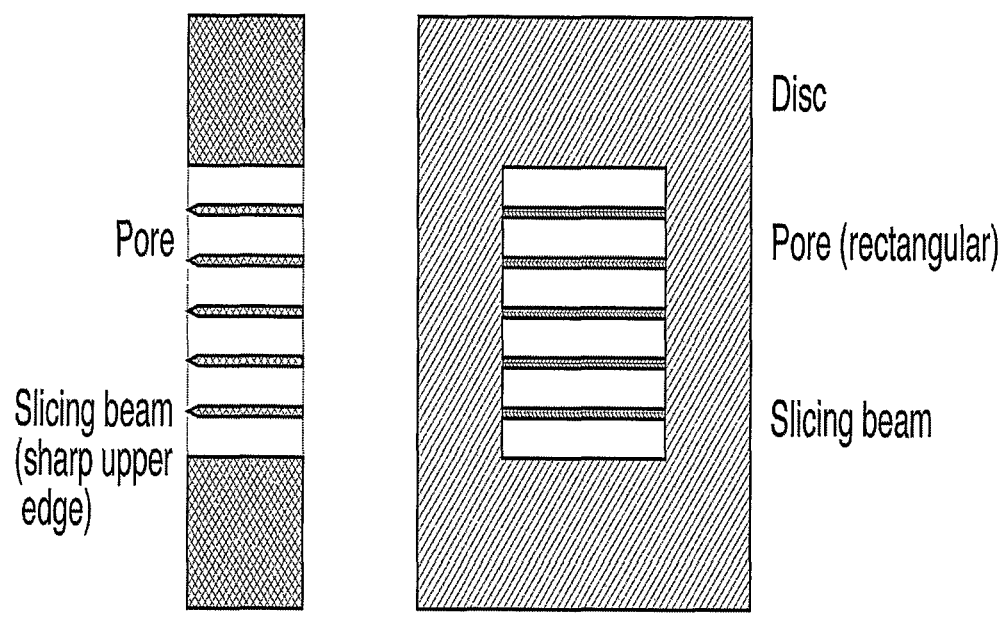
FIG. 1-5 are schematic presentations of different embodiments of the invention.

In the context of the present application and invention the following definitions apply:

The term "cell culture" is intended to mean the process by, and conditions under which viable cells or tissue is maintained under artificial conditions for short or long time outside of the organism from which it was originally isolated.

The term "cell aggregate" is intended to mean when two or more cells are attached to each other. This includes any artificial or naturally occurring aggregate or cluster of cells.

The term "tissue" in intended to mean any biological tissue, or part, or parts thereof obtained from a living organism, or artificially created from biological material, to mimic an organ or other type of organized biological material.

Examples are brain, liver, pancreatic tissue, or aggregates of nerve cells, muscle cells, liver cells, tumour cells, or different types of immature cells.

The term "biological material" is intended to mean any material consisting of eukaryotic or prokaryotic cells, or substances produced by such cells, or combinations of these two.

The term "splitting" is intended to mean the process by which a certain population of cells in culture in a given volume, is diluted to be grown in a larger volume, often by dividing the content of one culture flask in two or three, thereby decreasing the density of the cell culture.

The term "organotypic culture" is intended to mean cultures of cells, in which the cultures are established from thin sections of immature or mature tissue and not from dissociated cells. By culturing the slices under proper conditions, the organization of cells, typical for the particular organ can be maintained for weeks or months, creating an in vitro system closely mimicking the organ.

Description

The Microgrid and the Slicing Device

The invention relates to a biological material slicing device containing one or several microgrids. The microgrid, which may be a disc, comprises at least two pores having a size adopted to allow cells, cell aggregates, tissue or other biological material to pass through said pores, and a slicing beam separating said pores from each other, i.e., being placed in between said two pores, wherein biological material is split/sliced/cleaved into at least two parts when passing said microgrid. Said biological material may be a cell, cell aggregate, cell product, tissue, or piece of tissue, or organs, or parts thereof. Said slicing beam may have different or the same shape such as a sharp, rounded, blunt or arbitrarily shaped upper and/or lower edge. Said microgrid may have from 2 to about 1000 pores being separated by 1 to about 200 slicing beams, such as 1, 2, 4, 10, 100, 200. Said microgrid may have pores of a size from about 5 µm to 500 µm, such as 10, 50, 100, 200 µm. The dimensions of the slicing beam will depend on the application, such that the width may be ⅕-1/20 of the size of the pore and may be equal to the thickness. The height of the slicing beam may be equal the thickness of the microgrid. Said pores in a given microgrid may have the same size and form (rectangular, round etc) or different size and form. The size and form of the pores in a microgrid may also be different from the pores in another microgrid within the same slicing device.

Figure 2:
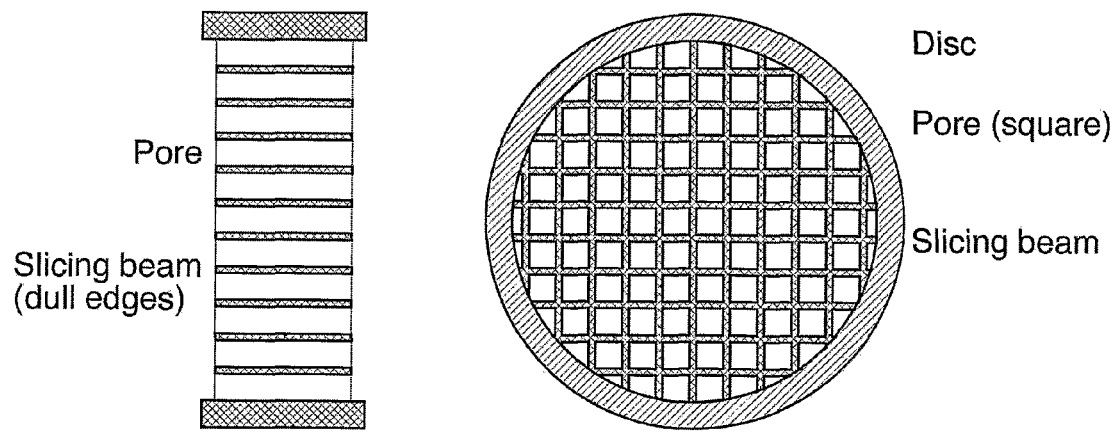
Figure 3:
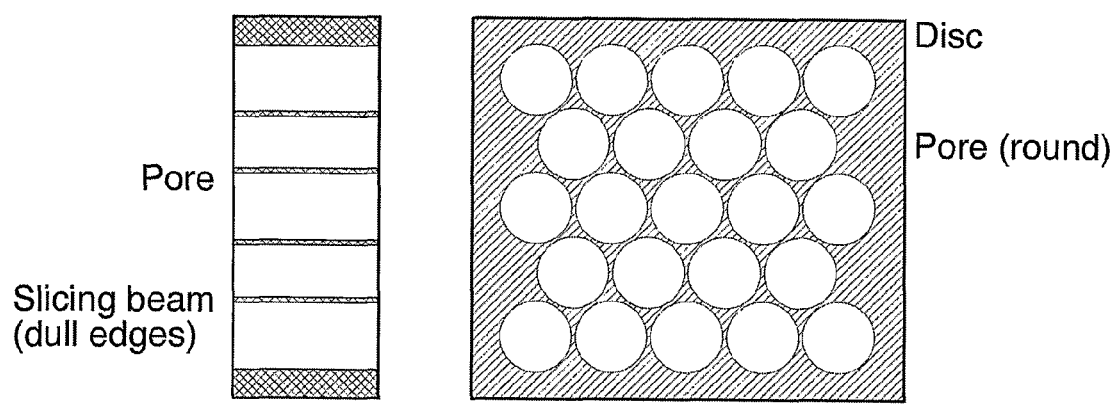

Said microgrid may be prepared from any suitable material such as a material selected from the group consisting of metals, glass, polymers, cheramics and silica or a mixture thereof. The microgrid may be coated/ligated with one or more components such as proteins, enzymes, lipids or mixtures thereof, or other material modifying the physical properties of the surface of the microgrid to optimize the interaction with the fluid and/or the cells/tissue passing through the microgrid. The slicing beams may be made to vibrate to enhance its function. Examples of micro-grids are shown in FIG. 1-3.

The invention also relates to a slicing device comprising at least one microgrid such as from 1 to 10 microgrids. For example 1, 2, 3, 4, 5, 6, 7, 8, 9 or 10 microgrids being the same or having different shapes, arranged to split/slice/cleave the biological specimen. It may have an in- and outlet to allow pieces of material to be transported through the microgrid(s). Other types of microgrids which can be used in a non-fluidic system may have other arrangements to allow for the tissue to be placed in an appropriate position relative the microgrid(s), thereby allowing it to be split/sliced/cleaved by the microgrid(s). The microgrid may be fixed within the slicing device, or move in any direction in relation to other microgrids or the slicing device, thereby enhancing its function.

Figure 4:
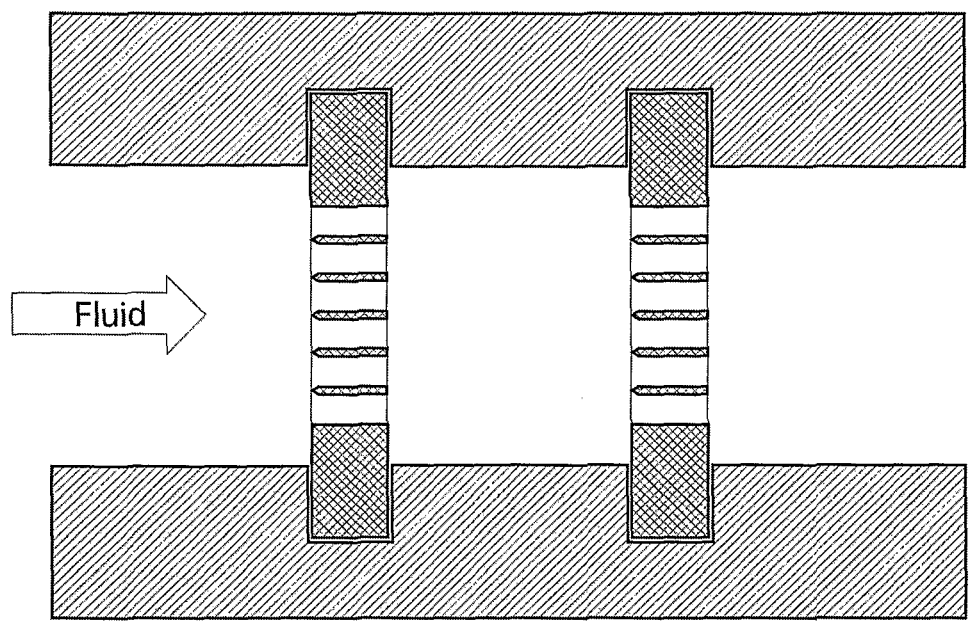
Figure 5:
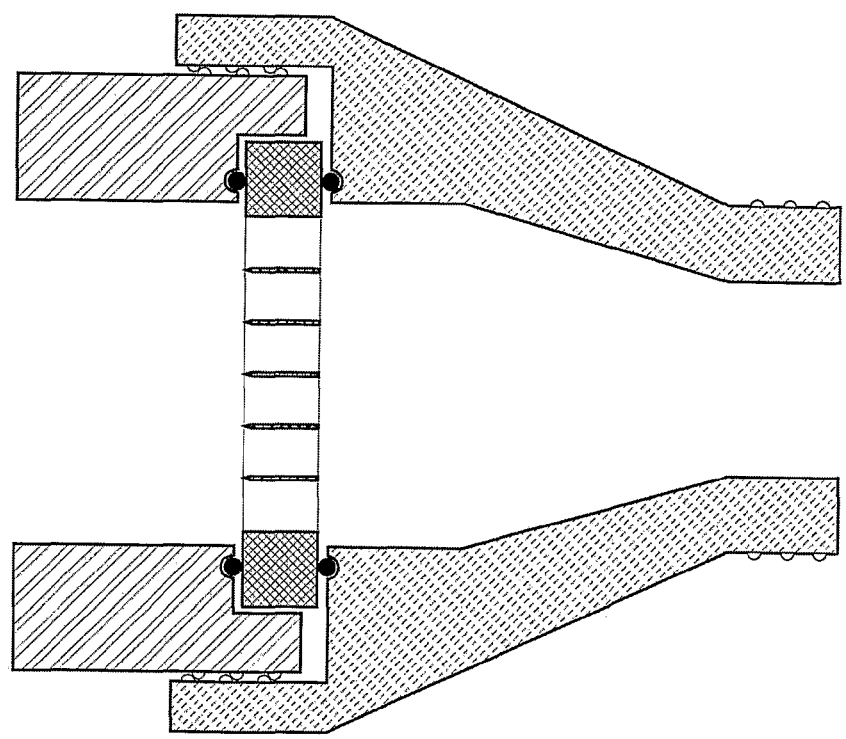
Figure 6A:
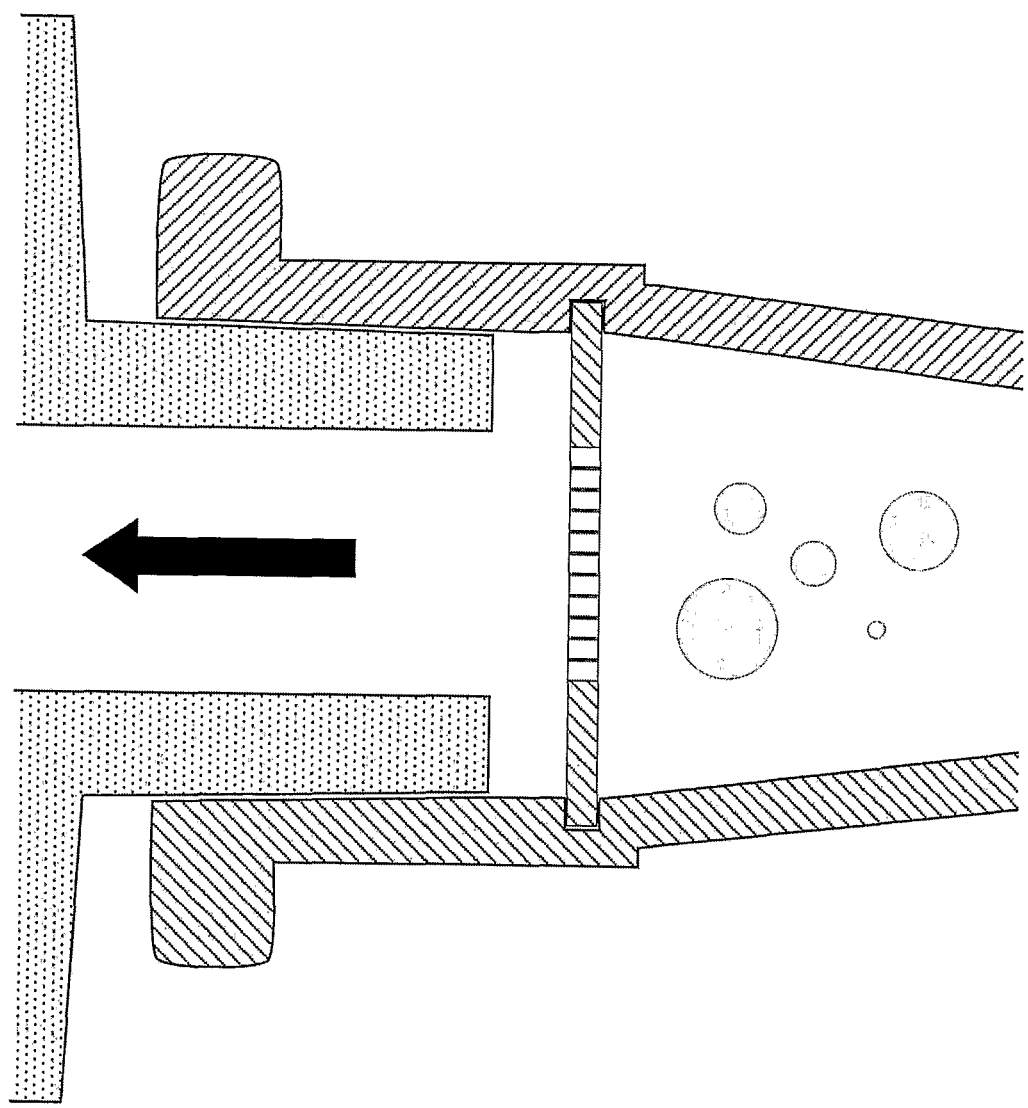
FIG. 6 shows how the cell clusters are passed through said microgrid mounted in a tissue device.
Figure 6B:
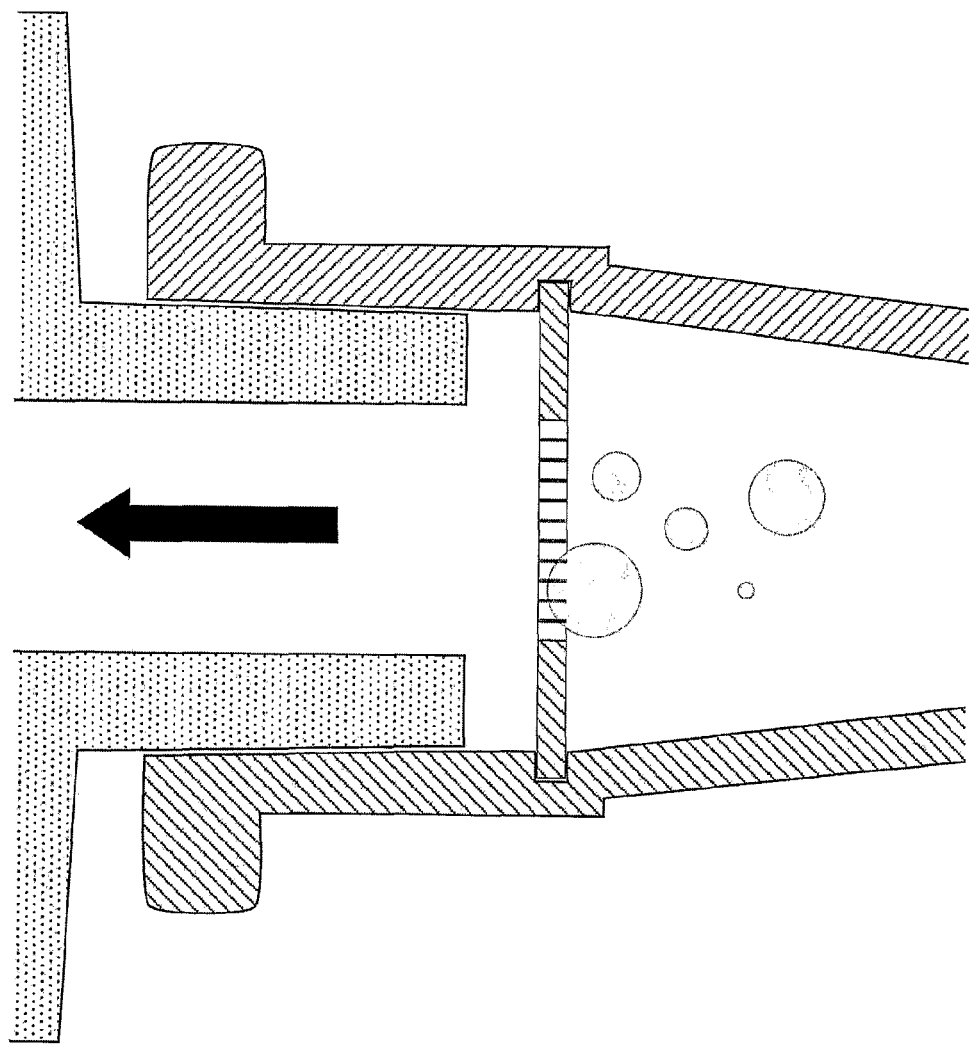
Figure 6C:
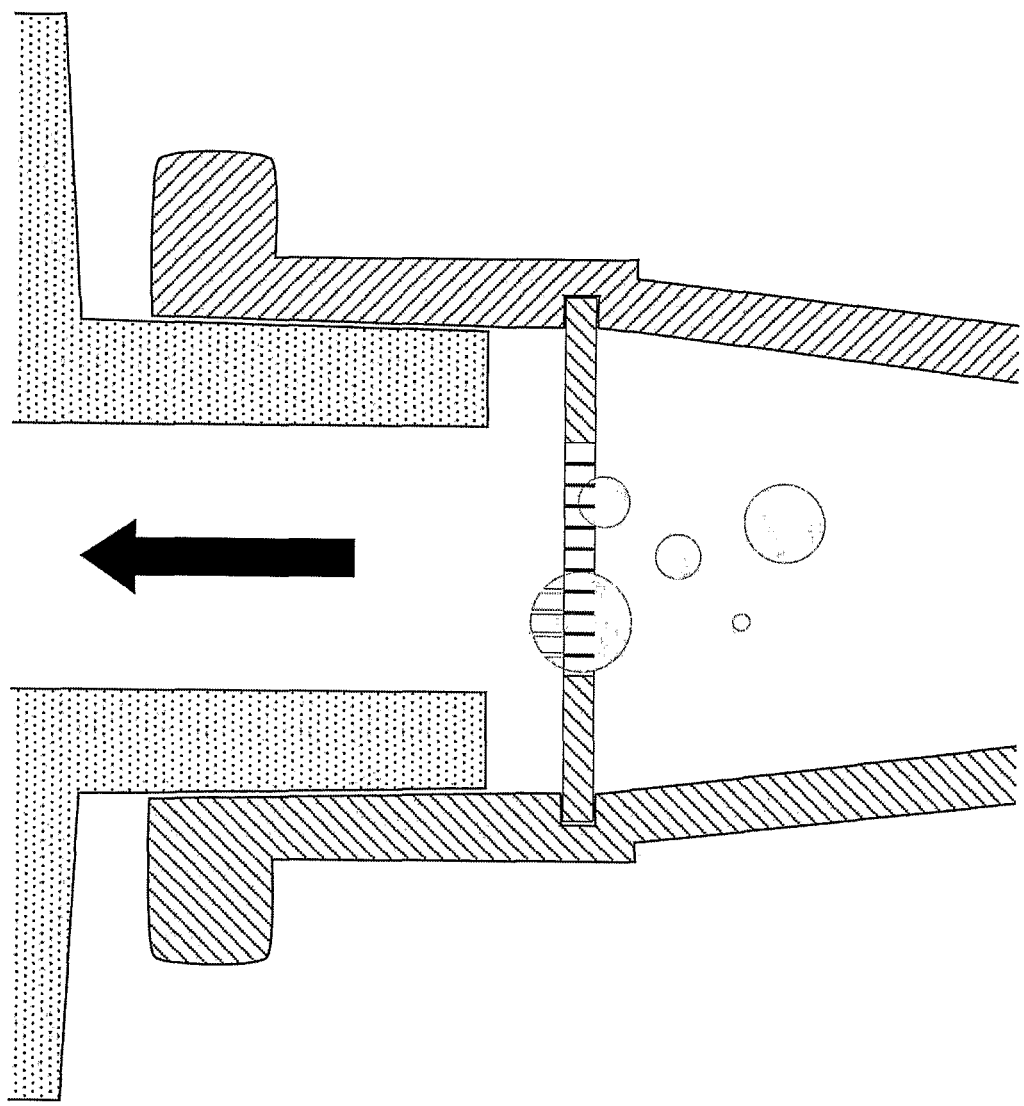
Figure 6D:
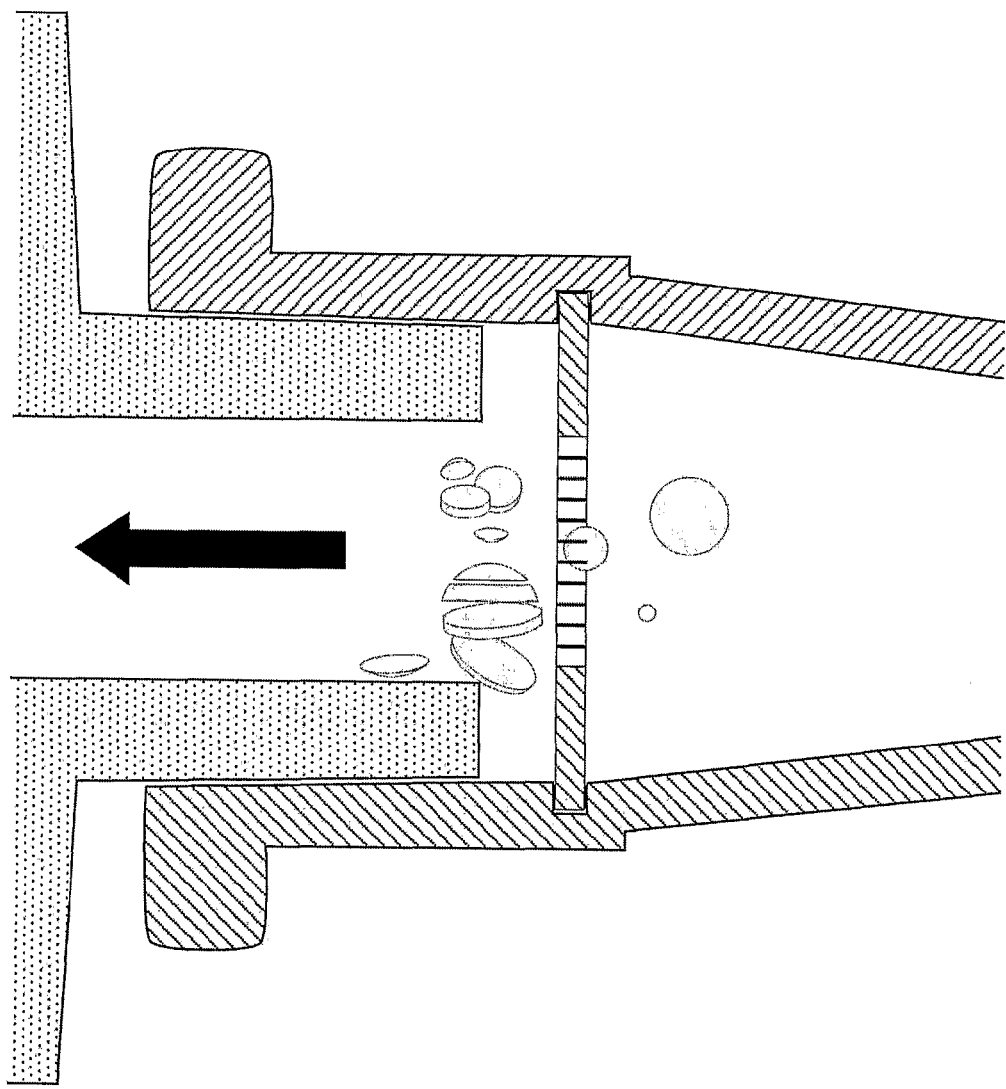

Examples of slicing devices are shown in FIG. 4-5.

The invention also relates to a slicing apparatus comprising one or more slicing devices through which biological material is passed, during which said biological material is sliced or cleaved into two or more parts. Said biological material may be a cell, cell aggregate, cell product, tissue, or piece of tissue, or organs, or parts thereof. One example being an apparatus to cleave clusters of cells during the passage of cultures of free-floating cell aggregates, wherein said slicing device containing one or more microgrids is embedded in a flow-through unit, wherein said flow-through unit is provided with a first and a second opening allowing cell aggregates and/or tissue to enter through said first opening, pass through one or two microgrids within the slicing device, and the resulting smaller cell clusters exit through the second opening. Said first and said second opening may have luer fittings to allow connection to syringes and tubings. To be able to slice or cleave said biological material, the apparatus comprises one or several microgrids. Said slicing apparatus comprises at least one microgrid with two or more pores of a size appropriate for the particular application. The slicing apparatus also contain in- and outlet, connections for tubing, a mechanism to aspirate and eject fluid, thereby forcing the biological tissue through the microgrid(s). To avoid deleteriously high pressure in the fluid, the slicing apparatus may be equipped with pressure sensors for feed-back control of the applied fluid pressure. This involves keeping control of both increased pressure when flushing cells or tissue through the device, and low pressure when aspirating cells or tissue. The above defined slicing device and slicing apparatus may be constructed as one unit or as a construction kit comprising at least one or more separate parts that upon use are assembled to one unit. One or more of the parts of said slicing device may be disposable.

The apparatus can be supplied with automated fluid handling. More specifically, automation concerns fluid flow control and applied pressure control to ensure optimal tissue homogenization conditions given a specific tissue type. Different automation protocols can be defined for each cell and culture type.

The slicing device as well as the apparatus as defined above may be used to cut tissue such as liver, brain, muscle, or cell aggregates such as free-floating neurospheres or other free-floating precursor cell aggregates in pieces or slices, of sizes appropriate for cell culture or other in vitro use, or to separate one or more cells from each other.

The invention also relates to the use of the slicing device or the apparatus as defined above to obtain cell clusters from organs, tissue, cell aggregates, such as stem cell cluster or embryonic stem cells.

Following examples are intended to illustrate, but not to limit, the invention in any manner, shape, or form, either explicitly or implicitly.

EXAMPLES

Example 1

A microgrid can be manufactured by convention microfabrication technologies. The desired projected shape of the microgrid is defined my photolithography on a silicon wafer, outlining multiple microgrids on a single silicon wafer. The exposed and developed wafer is subsequently subjected to wet or dry etching to produce the desired microstructures that compose the microgrid, with the desired beam widths and lengths and corresponding distance between beams. If other pore dimensions, round holes, square grid patterns etc. are desired this is accomplished by modifying the photolithographic mask. After the etch process the individual slicing devices are commonly released from the wafer by conventional wafer dicing saw equipment.

Example 2

One microgrid with a pore size of 100×500 μm and a width of the slicing beams of 30 μm is cast in a polymer cylinder with an inner diameter of 1.5 mm fitted at one end with a 15 cm long stainless steel tube, inner diameter 0.7 mm, and at the other end with an opening fitting on a standard plastic 10 ml sterile disposable syringe. By slowly aspirating and ejecting media containing free-floating cell aggregates through this device, the cell aggregates are sliced into smaller aggregates.

Example 3

Two replaceable microgrids with quadratic pores, size 10 μm, beam width 2 μm, placed in series in a cylinder with luer fittings at both ends. Cell aggregates or pieces of tissue are collected in fluid in a separate container, the pressure in the container increased to force the biological material through the two microgrids, thereby creating a suspension of single cells, without the need of enzymatic dissociation.

The invention claimed is:

1. A tissue or cell aggregate slicing apparatus comprising a slicing device, the slicing device comprising at least one microgrid, the microgrid made of silica, ceramics, or metal and comprising 2 to 1000 pores having a pore size of 50 to 200 μm and 2 to 200 slicing beams separating said pores from each other, said slicing beams having a width of 2.5 to 40 micrometers, a depth that is equal to a thickness of the microgrid, and sharp upper and/or lower edges forming a cutting edge for slicing tissue or cell aggregate;

wherein tissue or cell aggregate larger than the pores is sliced into at least two parts when passing said microgrid to form cell clusters comprising viable cells, the formed cell clusters having a width and height corresponding to dimensions of the pores;

wherein said slicing device is embedded in a flow-through unit, said flow-through unit comprising a first and a second opening allowing a stream of tissue or cell aggregate to enter through said first opening, pass through the microgrid within the slicing device, and the resulting cell clusters exit through the second opening;

wherein the pores have a rectangular shape; and wherein the cutting edge of the slicing beams is positioned in the stream to slice the tissue or cell aggregate into cell clusters as the stream passes through the microgrid.

2. A method of obtaining cell clusters from tissue or cell aggregates, comprising slicing the tissue or cell aggregates with a slicing apparatus according to claim 1 to obtain slices of cell clusters from the tissue or cell aggregates.

3. The slicing apparatus according to claim 1, wherein the microgrid is comprised of silica.

4. The slicing apparatus according to claim 3, wherein the microgrid comprises microstructures produced by wet or dry etching of a silicon wafer exposed and developed by photolithography.

5. A method for manufacturing a slicing apparatus according to claim 1, comprising defining a desired projected shape of the microgrid by photolithography on a silicon wafer, and subsequently subjecting the silicon wafer to wet or dry etching to produce microstructures that compose the microgrid, such that the microgrid comprises about 2 to about 1000 pores having a pore size of 50 to 200 μm and 2-200 slicing beams separating said pores from each other, said slicing beams having a width $\frac{1}{5}$ to $\frac{1}{20}$ of the size of the pores and sharp upper and/or lower edges, and the pores having a rectangular shape.

6. The slicing apparatus according to claim 1, comprising a pressure sensor to control fluid pressure through the microgrid to prevent deleteriously high pressure when aspirating the tissue or cell aggregate through the microgrid.

* * * * *